US009332909B2

(12) United States Patent
Kubo et al.

(10) Patent No.: US 9,332,909 B2
(45) Date of Patent: May 10, 2016

(54) FLUOROSCOPY APPARATUS

(71) Applicant: OLYMPUS CORPORATION, Tokyo (JP)

(72) Inventors: Kei Kubo, Tokyo (JP); Yasushige Ishihara, Tokyo (JP); Hiromi Shida, Tokyo (JP); Satoshi Takekoshi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 404 days.

(21) Appl. No.: 13/942,933

(22) Filed: Jul. 16, 2013

(65) Prior Publication Data

US 2014/0028824 A1   Jan. 30, 2014

(30) Foreign Application Priority Data

Jul. 25, 2012 (JP) ................................. 2012-164924

(51) Int. Cl.
| | |
|---|---|
| *H04N 7/18* | (2006.01) |
| *A61B 5/00* | (2006.01) |
| *A61B 1/04* | (2006.01) |
| *A61B 1/00* | (2006.01) |
| *A61B 1/06* | (2006.01) |

(52) U.S. Cl.
CPC ........... *A61B 5/0071* (2013.01); *A61B 1/00009* (2013.01); *A61B 1/043* (2013.01); *A61B 1/0638* (2013.01); *A61B 1/0646* (2013.01)

(58) Field of Classification Search
None
See application file for complete search history.

(56) References Cited

U.S. PATENT DOCUMENTS

| | | | | |
|---|---|---|---|---|
| 2004/0109231 | A1* | 6/2004 | Haisch ................. | A61B 5/0066 359/385 |
| 2006/0074893 | A1* | 4/2006 | Snijder .............. | G06K 9/00711 |
| 2007/0250274 | A1* | 10/2007 | Volkov ................ | C12Q 1/6813 702/22 |
| 2009/0305287 | A1* | 12/2009 | Nordman ............. | C12Q 1/6869 435/6.12 |
| 2012/0248333 | A1* | 10/2012 | Fallert ................ | A61B 1/00186 250/458.1 |

FOREIGN PATENT DOCUMENTS

JP        3771985 B2    5/2006

OTHER PUBLICATIONS

English Abstract only of corresponding JP 10-201700, dated Aug. 4, 1998.

* cited by examiner

*Primary Examiner* — Frederick Bailey
(74) *Attorney, Agent, or Firm* — Scully, Scott, Murphy & Presser, P.C.

(57) ABSTRACT

Provided is a fluoroscopy apparatus including a fluorescence-image generating portion that generates a fluorescence image; an identifying portion that identifies a position of a high-luminance region in the fluorescence image; a storage portion that stores the position of the high-luminance region; a detecting portion that detects an amount of change in a physical quantity, which can possibly act as a cause of changes in a property of the high-luminance region, starting from a time at which the position of the high-luminance region is identified by the identifying portion; a confidence-level calculating portion that calculates a confidence level of the property of the high-luminance region based on the detected amount of change; and a display-image generating portion that generates a display image in which the display mode at the position of the high-luminance region is set in accordance with the confidence level.

14 Claims, 12 Drawing Sheets

FLUOROSCOPY APPARATUS

CROSS-REFERENCE TO RELATED APPLICATIONS

This application claims the benefit of Japanese Patent Application No. 2012-164924, the content of which is incorporated herein by reference.

TECHNICAL FIELD

The present invention relates to a fluoroscopy apparatus.

BACKGROUND ART

In the related art, there is a known fluoroscopy apparatus that radiates excitation light onto a biological subject to cause emission of fluorescence from a diseased portion contained in the biological subject, that captures the fluorescence, and that observes the diseased portion in an acquired fluorescence image in the form of a high-luminance region (for example, see Patent Literature 1).

CITATION LIST

Patent Literature

{Patent Literature 1} Publication of Japanese Patent No. 3771985

SUMMARY OF INVENTION

The present invention provides a fluoroscopy apparatus including a light source that radiates excitation light onto an observation subject; a fluorescence-image generating portion that generates a fluorescence image by capturing fluorescence generated at the observation subject due to irradiation with the excitation light from the light source; an identifying portion that identifies a position of a high-luminance region that has a luminance value equal to or greater than a predetermined threshold in the fluorescence image generated by the fluorescence-image generating portion; a storage portion that stores the position of the high-luminance region identified by the identifying portion; a detecting portion that detects an amount of change in a physical quantity, which can possibly act as a cause of changes in a property of the high-luminance region, starting from a time at which the position of the high-luminance region is identified by the identifying portion; a confidence-level calculating portion that calculates a confidence level of the property of the high-luminance region identified by the identifying portion based on the amount of change detected by the detecting portion; and a display-image generating portion that generates a display image in which the display mode at the position of the high-luminance region stored in the storage portion is set in accordance with the confidence level calculated by the confidence-level calculating portion.

DESCRIPTION OF EMBODIMENT

A fluoroscopy apparatus 1 according to a first embodiment of the present invention will be described below with reference to FIGS. 1 to 7.

Figure 1:
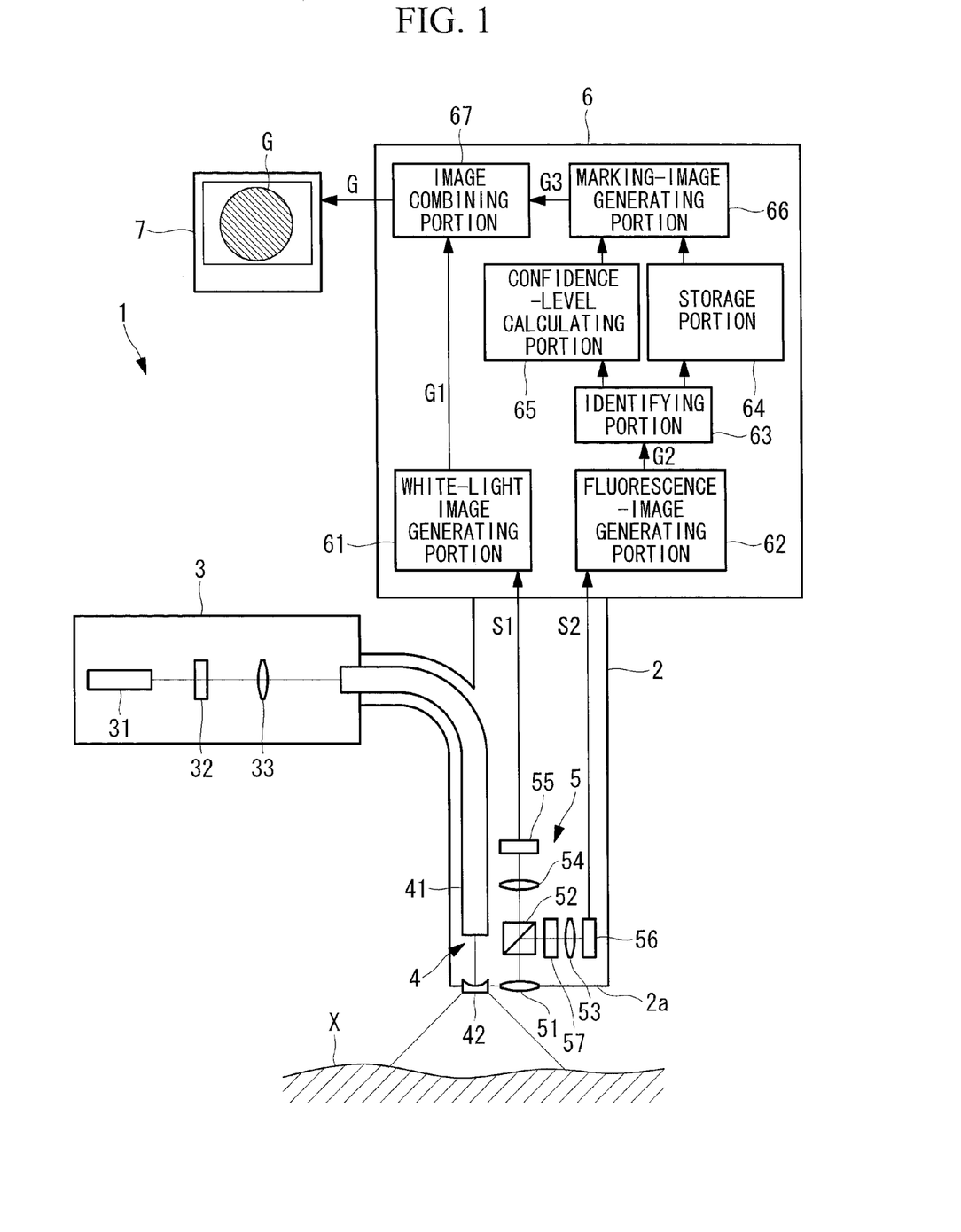
FIG. 1 is an overall configuration diagram of a fluoroscopy apparatus according to a first embodiment of the present invention.

As shown in FIG. 1, the fluoroscopy apparatus 1 according to this embodiment is an endoscope apparatus and is provided with a long, thin inserted portion 2 that is inserted into a body; a light source 3; an illumination unit 4 that radiates excitation light and white light (reference light) from the light source 3 toward an observation subject X from a distal end 2a of the inserted portion 2; an image-acquisition unit 5 that is provided at the distal end 2a of the inserted portion 2 and that acquires image information S1 and S2 about biological tissue, that is, the observation subject X; an image processing unit 6 that is disposed at the base end of the inserted portion 2 and that processes the image information S1 and S2 acquired by the image-acquisition unit 5; and a display portion 7 that displays a combined image G processed by the image processing unit 6.

The light source 3 is provided with a xenon lamp 31, a filter 32 that extracts the excitation light and white light (illumination light: wavelength band from 400 nm to 740 nm) from light emitted from the xenon lamp 31, and a coupling lens 33 that focuses the excitation light and white light extracted by the filter 32.

The illumination unit 4 is provided with a light-guide fiber 41 that is disposed over nearly the entire length of the inserted portion 2 in the longitudinal direction thereof, and an illumination optical system 42 provided at the distal end 2a of the inserted portion 2. The light-guide fiber 41 guides the excitation light and the white light focused by the coupling lens 33. The illumination optical system 42 spreads out and radiates the excitation light and white light guided thereto by the light-guide fiber 41 onto the observation subject X facing the distal end 2a of the inserted portion 2.

The image-acquisition unit 5 is provided with an objective lens 51 that collects light returning from a predetermined observation area of the observation subject X; a dichroic mirror 52 that, of the light collected by the objective lens 51, reflects light having a wavelength equal to or greater than the excitation wavelength (excitation light and fluorescence) and allows white light (return light) having a shorter wavelength than the excitation wavelength to pass therethrough; two focusing lenses 53 and 54 that focus the fluorescence reflected by the dichroic mirror 52 and the white light that has passed through the dichroic mirror 52, respectively; and two image-acquisition devices 55 and 56, like CCDs or CMOS devices, that capture the white light and the fluorescence focused by the focusing lenses 53 and 54.

The image-acquisition devices 55 and 56 acquire white-light image information S1 and fluorescence image information S2, respectively.

In the figures, reference sign 57 indicates an excitation light cut filter that blocks the excitation light in the light reflected by the dichroic mirror 52 (it allows only the light having, for example, a wavelength band from 760 nm to 850 nm, to pass therethrough).

The image processing unit 6 is provided with a white-light image generating portion (reference-image generating portion) 61 that generates a white-light image (reference image) G1 from the white-light image information S1 acquired by the image-acquisition device 55; a fluorescence-image generating portion 62 that generates a fluorescence image G2 from the fluorescence image information S2 acquired by the image-acquisition device 56; an identifying portion 63 that, from the fluorescence image G2 generated by the fluorescence-image generating portion 62, identifies the positions of pixels having luminance values equal to or greater than a threshold set in advance; a storage portion 64 that stores the positions of the pixels identified by the identifying portion 63; a confidence-level calculating portion (detecting portion) 65 that calculates the confidence level of properties possessed by the pixels identified by the identifying portion 63; a marking-image generating portion (display-image generating portion) 66 that generates a marking image (display image) G3 having hues in accordance with the confidence level calculated by the confidence-level calculating portion 65 at the pixels whose positions are stored in the storage portion 64; and an image combining portion 67 that generates a combined image G by superimposing the white-light image G1 on the marking image G3.

The identifying portion 63 compares luminance values of individual pixels of the fluorescence image G2 input thereto from the fluorescence-image generating portion 62 with the predetermined threshold, identifies pixels having luminance values equal to or greater than the predetermined threshold as high-luminance regions P, and outputs the positions of the identified pixels to the storage portion 64. In addition, the identifying portion 63 outputs a trigger signal to the confidence-level calculating portion 65 at the same time as it outputs the positions of the pixels to the storage portion 64.

The storage portion 64 stores pixel positions input from the identifying portion 63. Each time new pixel positions are input from the identifying portion 63, the storage portion 64 updates the pixel positions stored up to that point with the new pixel positions. By doing so, the storage portion 64 stores the most recent positions of the high-luminance regions P. The storage portion 64 outputs the pixel positions to the marking-image generating portion 66 at the update timing.

The confidence-level calculating portion 65 has a timer, and, upon receiving the input of the trigger signal from the identifying portion 63, it starts measuring time with the timer by using that input as a trigger. Then, the confidence-level calculating portion 65 calculates the confidence level of the properties of the high-luminance regions P based on the elapsed time (amount of change) measured by the timer. By doing so, the confidence level is calculated for the properties of the high-luminance regions P that can change due to the passage of time (physical quantity), such as, for example, the positions and luminance values of the high-luminance regions P. The confidence-level calculating portion 65 outputs the calculated confidence level to the marking-image generating portion 66.

Figure 2:
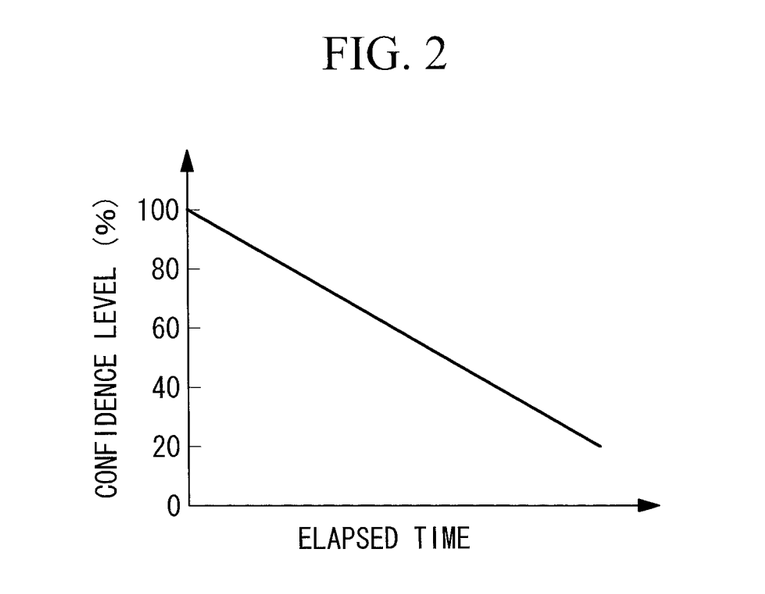
FIG. 2 is a graph showing a function for deriving a confidence level based on the elapsed time since the time at which a high-luminance region is identified.

As shown in FIG. 2, the confidence level of the properties of the high-luminance regions P is calculated in accordance with a function that linearly decreases with an increase in the elapsed time. By doing so, it is possible to calculate the confidence level of the property of the high-luminance region P by means of a simple calculation. The slope of this function may be arbitrarily set by a user or it may be set based on the relationship measured in advance between the elapsed time and the amount of change in the positions of the high-luminance regions P. Each time a new trigger signal is input from the identifying portion 63, the confidence-level calculating portion 65 resets the elapsed time measured by the timer to zero and restarts the measurement of time from zero.

The marking-image generating portion 66 holds a hue scale in which the confidence level and hue are associated with each other. From the hue scale, the marking-image generating portion 66 selects a hue that corresponds to the confidence level input from the confidence-level calculating portion 65 and generates the marking image G3 by applying the selected hue to the pixel positions input from the storage portion 64.

Next, the effect of the thus-configured fluoroscopy apparatus 1 will be described.

To observe biological tissue in a body, that is, the observation subject X, by using the fluoroscopy apparatus 1 according to this embodiment, the inserted portion 2 is inserted into the body, and the distal end 2a of the inserted portion 2 is made to face the observation subject X. Then, the excitation light and the white light are generated by activating the light source 3 and are made to enter the light-guide fiber 41 by means of the coupling lens 33. The excitation light and the white light that have reached the distal end 2a of the inserted portion 2 by being guided through the light-guide fiber 41 are spread out and radiated onto the observation subject X by the illumination optical system 42.

A fluorescent substance contained inside the observation subject X is excited by the excitation light, thus generating fluorescence, and the white light is also reflected at a surface of the observation subject X. The fluorescence and the reflected white light return to the distal end 2a of the inserted portion 2 from the observation subject X, and the fluorescence and the white light generated in the observation area, representing a portion of the observation subject X, are collected by the objective lens 51.

Figure 3:
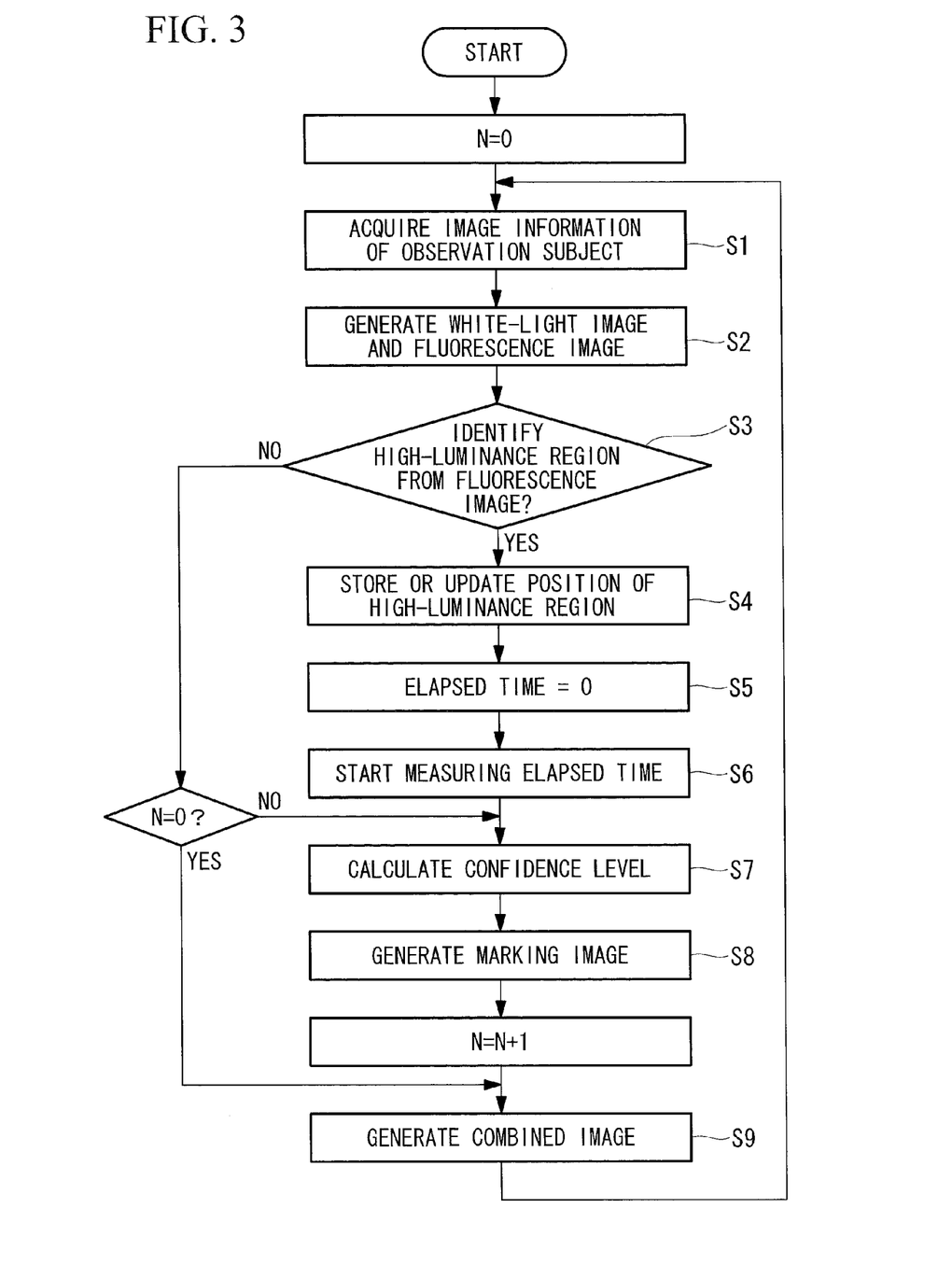
FIG. 3 is a flowchart for explaining the operation of the fluoroscopy apparatus in FIG. 1.

FIG. 3 shows a flowchart for explaining processing performed by the fluoroscopy apparatus 1 according to this embodiment for generating the combined image G.

The fluorescence and the white light collected by the objective lens 51 are split by the dichroic mirror 52 in accordance with the wavelengths thereof; for example, the white light in the wavelength band from 400 nm to 700 nm is focused by the focusing lens 54 and is acquired by the image-acquisition device 55 in the form of the white-light image information S1 (Step S1).

In addition, of the light reflected by the dichroic mirror 52, for example, light in the wavelength band from 700 nm to 850 nm, including the excitation light and the fluorescence in the fluorescence and the white light collected by the objective lens 51, only the fluorescence is focused by the focusing lens 53, after removing the excitation light (for example, light at 740 nm or less) by the excitation light cut filter 57, and the fluorescence is acquired by the image-acquisition device 56 in the form of the fluorescence image information S2 (Step S1).

The image information S1 and S2 acquired by the individual image-acquisition devices 55 and 56 is transmitted to the image processing unit 6. At the image processing unit 6, the white-light image information S1 is input to the white-light image generating portion 61, where the white-light image G1 is generated (Step S2). On the other hand, the fluorescence image information S2 is input to the fluorescence-image generating portion 62, where the fluorescence image G2 is generated (Step S2).

The generated fluorescence image G2 is transmitted to the identifying portion 63, and the positions of the high-luminance regions P having luminance values equal to or greater than the predetermined threshold are identified (Step S3). If high-luminance regions P do not exist (NO in Step S3), the white-light image G1 is displayed on the display portion 7 as the combined image G without modification (Step S9), and the process returns to Step S1.

If the high-luminance regions P exist (YES in Step S3), the identified positions of the high-luminance regions P are output to the storage portion 64 from the identifying portion 63 and are stored in the storage portion 64 (Step S4). Simultaneously, the trigger signal is output to the confidence-level calculating portion 65 from the identifying portion 63; the timer at the confidence-level calculating portion 65 starts to measure the elapsed time (Steps S5 and S6); the confidence level of the properties of the high-luminance regions P are calculated from the measured elapsed time (Step S7); and the calculated confidence level is output to the marking-image generating portion 66. Then, at the marking-image generating portion 66, the marking image G3 having hues corresponding to the confidence level input from the confidence-level calculating portion 65 at the positions of the high-luminance regions P is generated (Step S8).

Note that, in FIG. 3, N is a number that indicates the order of the fluorescence images G2 in which the high-luminance regions P are identified. In other words, N remains 0 until a high-luminance region P is identified for the first time after the acquisition of the image information S1 and S2 has started, and thus, processing from Steps S4 to S8 is not performed during this time. Subsequently, processing from Steps S4 to S8 is started when a high-luminance region P is identified, and N is incremented each time a high-luminance region P is identified in the fluorescence images G2.

At the image combining portion 67, the white-light image G1 transmitted thereto from the white-light image generating portion 61 is superimposed on the marking image G3 (Step S9), and the generated combined image G is output to the display portion 7 from the image combining portion 67. When there is a period of time during which the high-luminance regions P are not identified in the fluorescence image G2 (NO in Step S3), the hues of the high-luminance regions P in the combined image G change over time with a decrease over time in the confidence level calculated by the confidence-level calculating portion 65, as shown in (a) to (c) in FIG. 4. Different hatching directions in (a) to (d) in FIG. 4 indicate different hues. In addition, (a) to (d) in FIG. 4 show combined images G captured by causing a liquid containing a fluorescent substance to flow in a ureter (see broken line) existing in the observation subject X.

Figure 4:
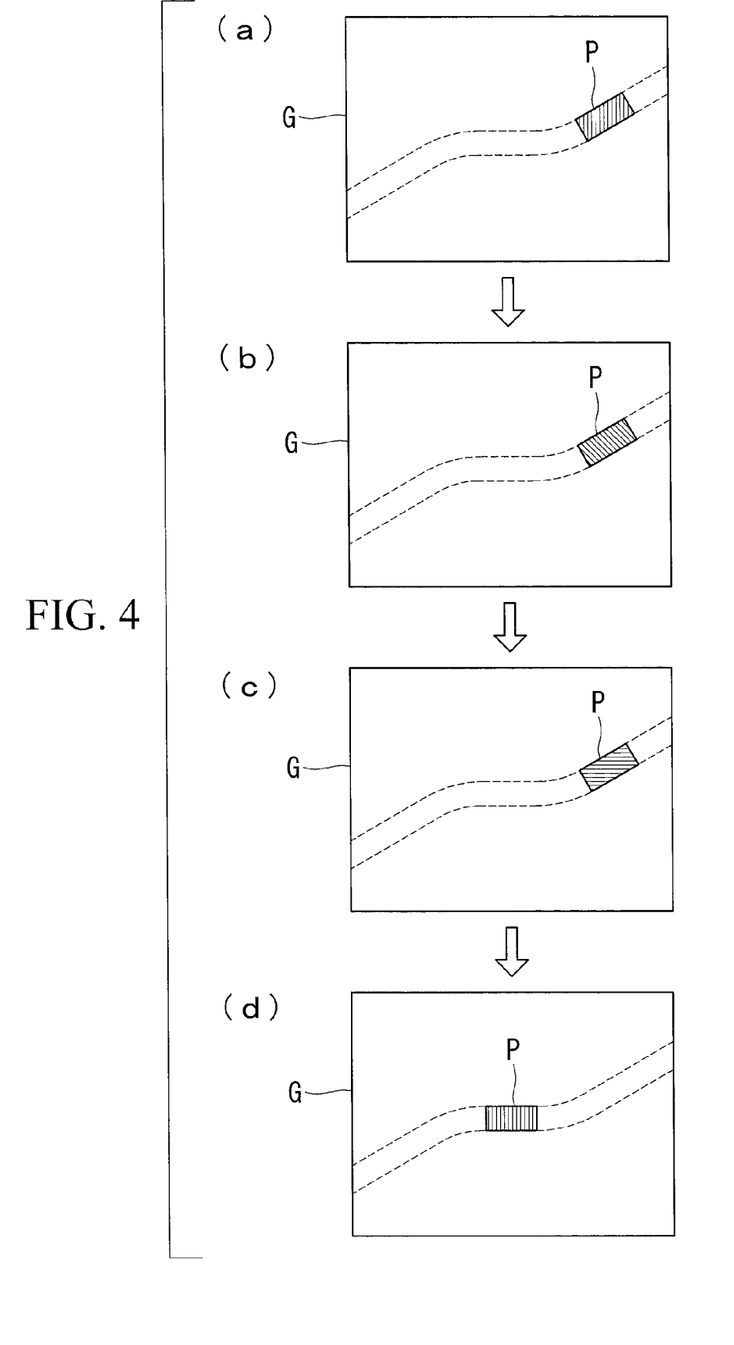
FIG. 4 is a diagram showing combined images time-sequentially generated by the fluoroscopy apparatus in FIG. 1.

Then, when new high-luminance regions P are identified by the identifying portion 63 (YES in Step S3), by updating the positions of the high-luminance regions P stored in the storage portion 64 (Step S4), the positions of the high-luminance regions P in the combined image G are updated to the most recent positions, as shown in (d) in FIG. 4. At this time, the elapsed time measured by the timer at the confidence-level calculating portion 65 is reset to zero, and thus, the confidence level is calculated to be 100%, which also restores the hues of the high-luminance regions P to the initial hue; if high-luminance regions P are not identified thereafter, the hues of the high-luminance regions P change over time.

In this case, for example, if a liquid containing a fluorescent substance is made to flow in a ureter contained in the observation subject X, the high-luminance regions P are identified intermittently due to a discontinuous flow of the liquid in the ureter. In this way, when there is a gap in time between the last time the high-luminance regions P are identified and the next time the high-luminance regions P are identified, the high-luminance regions P identified last time continue to be displayed in the combined image G. During a period in which this combined image G is displayed, the positions of the high-luminance regions P displayed in the current combined image G may become shifted from the actual positions of the high-luminance regions P due to relative positional shifting between the distal end 2a of the inserted portion 2 and the observation subject X.

With the fluoroscopy apparatus 1 according to this embodiment, the confidence level of the positions of the high-luminance regions P, which decreases with the elapsed time since the time at which the positions of the high-luminance regions P are identified, is reflected in the hues of the high-luminance regions P. There is an advantage in that a user can recognize the degree by which the positions of the high-luminance regions P displayed in the current combined image G may possibly be shifted from the actual positions of the high-luminance regions P based on the hues thereof, and thus, he/she can properly interpret the positions of the high-luminance regions P displayed in the current combined image G.

Note that, instead of the hue scale, the marking-image generating portion 66 in this embodiment may hold a saturation scale in which the confidence level is associated with the saturation or a brightness scale in which the confidence level is associated with the brightness, and the marking-image generating portion 66 may select the saturation or the brightness that corresponds to the confidence level. In this case, the saturation or the brightness of the high-luminance regions P in the combined image G changes in accordance with the confidence level.

Figure 5:
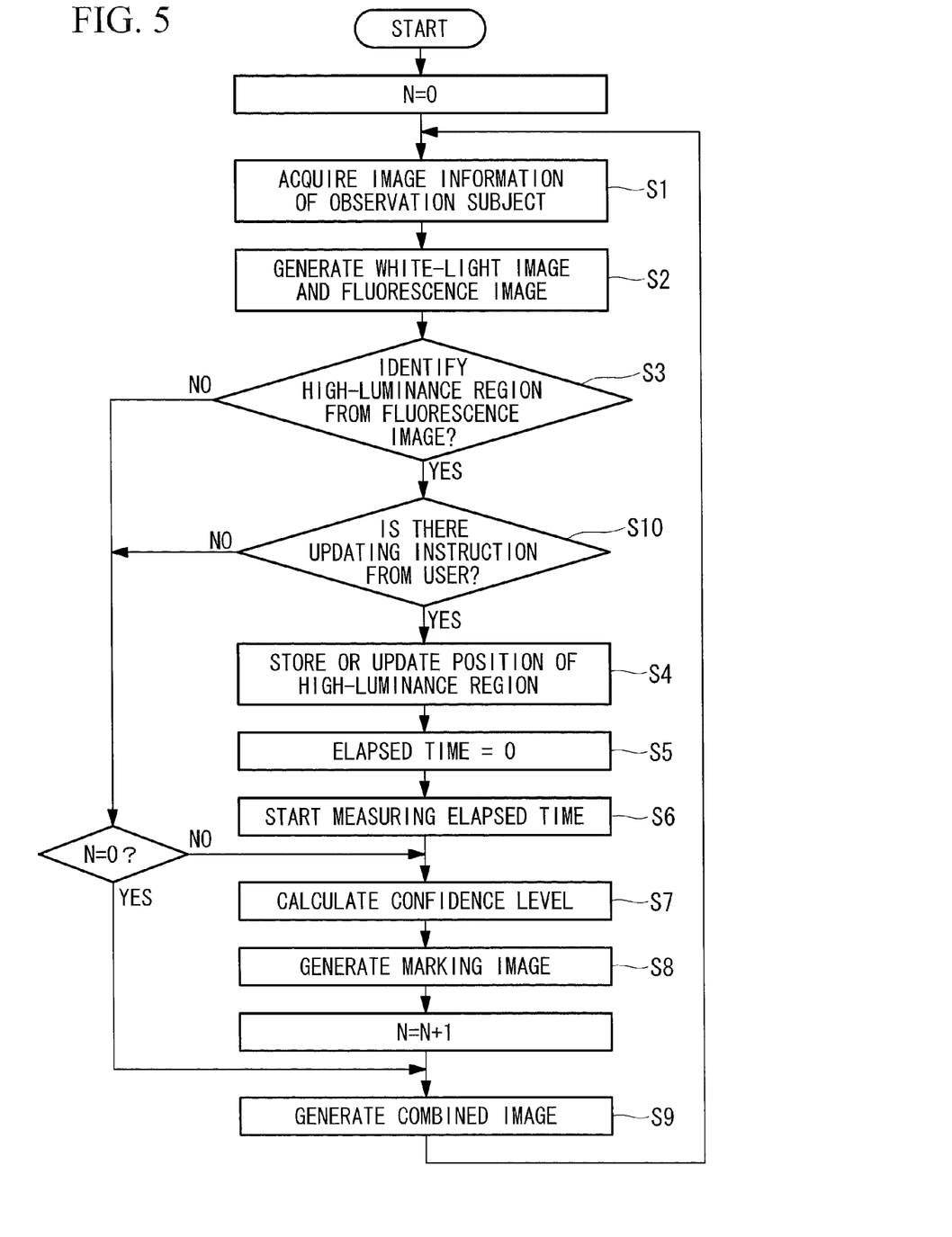
FIG. 5 is a flowchart for explaining a modification of the operation of the fluoroscopy apparatus in FIG. 1.

In addition, the confidence-level calculating portion 65 in this embodiment resets the elapsed time measured by the timer to zero each time a new trigger signal is input from the identifying portion 63 and restarts the measurement of time from zero; alternatively, however, the measurement of time may be restarted from zero in accordance with an instruction from the user (Step S10), as shown in FIG. 5. By doing so, it is possible to continuously measure the elapsed time of the identified high-luminance regions not only in the case in which fluorescence is generated discontinuously, like the case of the ureter, but also in the case in which fluorescence is continuously observed over a certain period of time, like the case of fluorescence in a tumor region.

Figure 6:
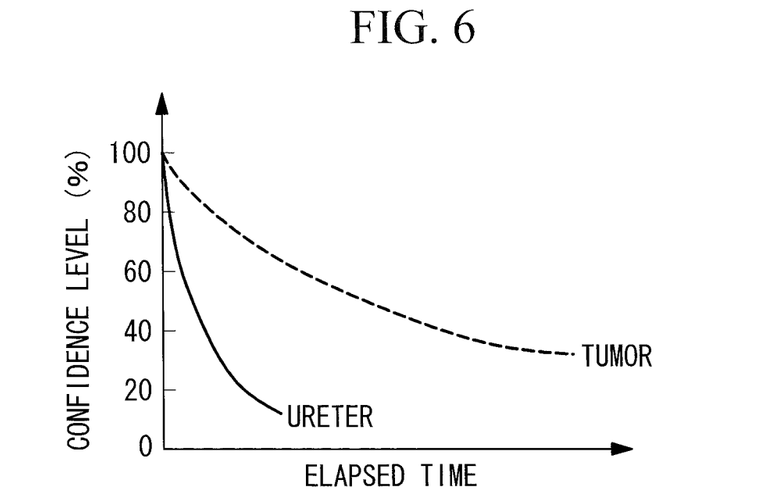
FIG. 6 is a graph showing a modification of the function for deriving the confidence level based on the elapsed time since the time at which the high-luminance region is identified.

In addition, in this embodiment, although a function that linearly decreases with an increase in the elapsed time is used as the function for deriving the confidence level, the user can set an appropriate function in advance. Furthermore, a different function may be set for each portion of the observation subject X. In FIG. 6, as portions of the observation subject X, a tumor and a ureter to be surgically observed are shown.

For example, because the fluorescence from the ureter is discontinuously observed, the degree by which the confidence level decreases for the same amount of elapsed time may be higher than in the case where the tumor is observed. Accordingly, for example, if the display mode is such that the confidence level is lower when the user treats the peripheries of the ureter, the user can temporarily stop the treatment and restart the treatment the next time the fluorescence from the ureter is observed and the confidence level is reset to 100%. Accordingly, it becomes possible to perform the treatment always in a state in which the confidence level is high based on the display mode. In this case, the fluoroscopy apparatus 1 is provided with an input portion (not shown) in which the user specifies portions of the observation subject X, and a function for the observation subject X specified via the input portion is used for calculating the confidence level.

In addition, in this embodiment, the storage portion 64 may sequentially and continuously store the positions of the high-luminance regions P input from the identifying portion 63 for a predetermined number of times (for example, ten times), the storage portion 64 may output all of the stored positions of the high-luminance regions P to the marking-image generating portion 66, and the marking-image generating portion 66 may generate marking images G3 having hues in accordance with the confidence level at all of the positions of the high-luminance regions P input from the storage portion 64.

Figure 7:
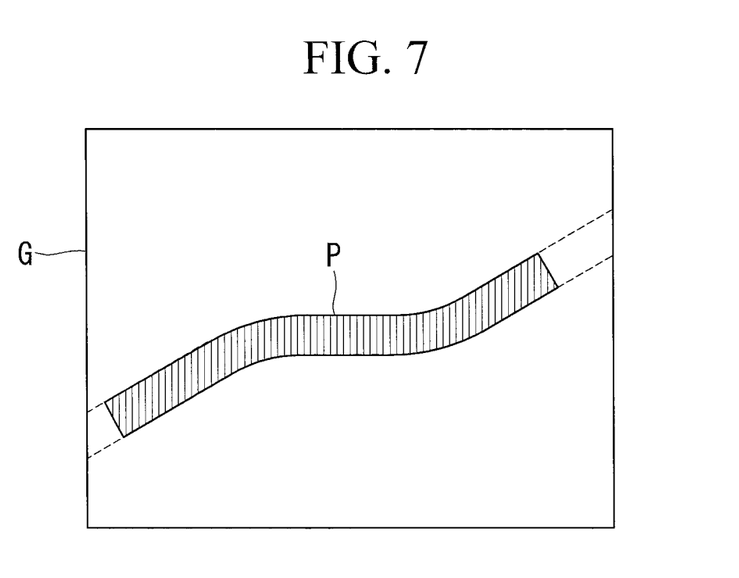
FIG. 7 is a diagram showing a modification of the combined image generated by the fluoroscopy apparatus in FIG. 1.

By doing so, when the high-luminance regions P have moved in the fluorescence image G2 due to the movement of a fluorescent substance in the observation subject X, marking images G3 in which the movement paths thereof are shown as high-luminance regions P are generated, as shown in FIG. 7. Therefore, in the marking images G3, it is easy to identify the shape of an organ in which a fluorescent substance has moved, such as the ureter.

Next, a fluoroscopy apparatus 100 according to a second embodiment of the present invention will be described with reference to FIGS. 8 to 10.

Figure 8:
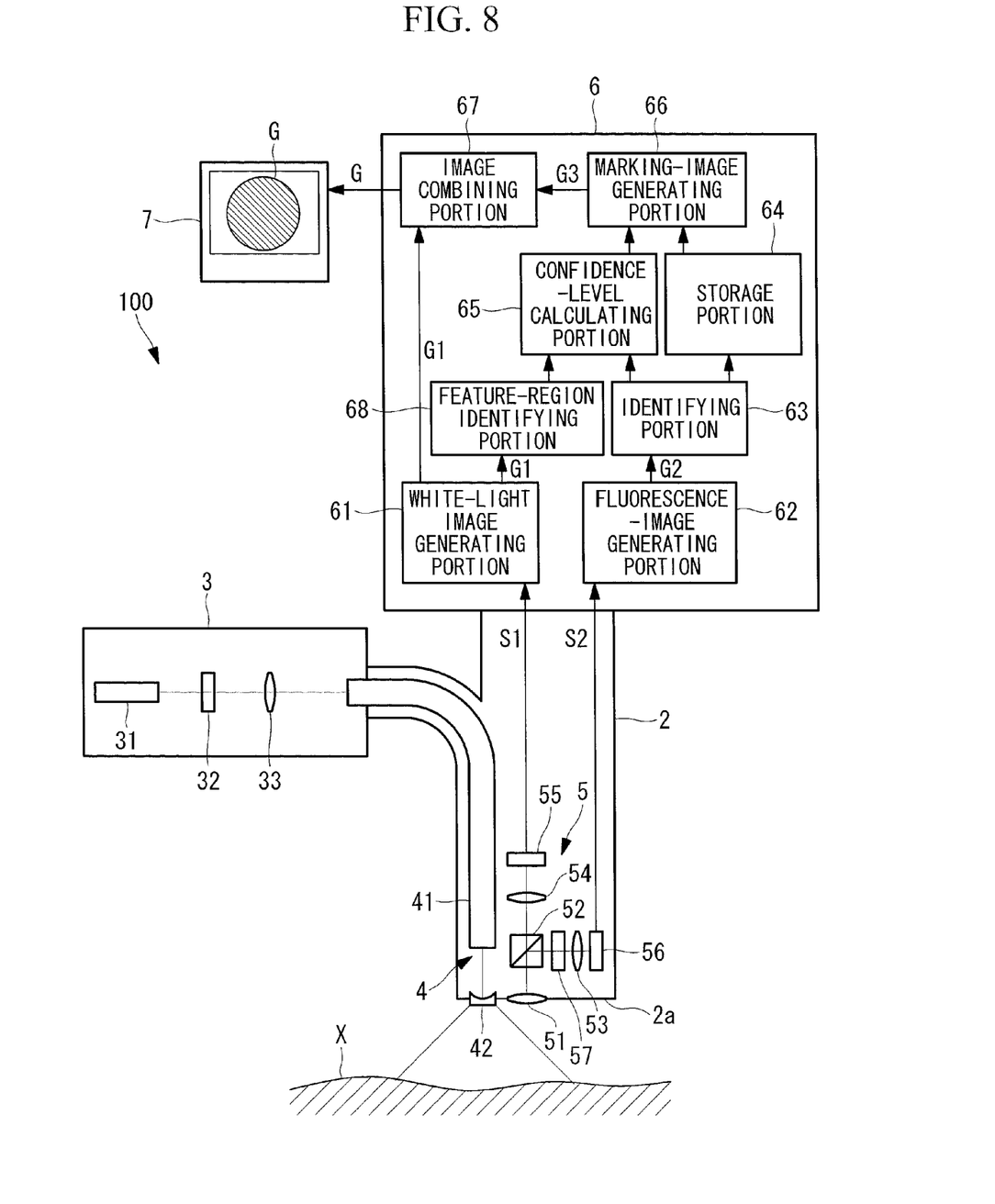
FIG. 8 is an overall configuration diagram of a fluoroscopy apparatus according to a second embodiment of the present invention.

As shown in FIG. 8, the fluoroscopy apparatus 100 according to this embodiment differs from the fluoroscopy apparatus 1 according to the first embodiment in that the image processing unit 6 is provided with a feature-region identifying portion 68 that identifies a feature region of the observation subject X in the white-light image G1, and that the confidence-level calculating portion 65 calculates the confidence level in consideration of an amount of movement (amount of change) of relative positions (physical quantity) between the observation subject X and the distal end 2*a* of the inserted portion 2, instead of the elapsed time measured by the timer, or in addition to the elapsed timer. Therefore, in this embodiment, processing performed by the feature-region identifying portion 68 and the confidence-level calculating portion 65 will mainly be described, and description of the configuration in common with the first embodiment will be omitted.

The feature-region identifying portion 68 stores a region in which specific tissue or the like is captured in the white-light image G1 input from the white-light image generating portion 61 as a feature region. Then, by comparing a new white-light image G1 input from the white-light image generating portion 61 and the stored feature region, the feature-region identifying portion 68 detects the position of the feature region in that white-light image G1, and outputs the position of the detected feature region to the confidence-level calculating portion 65.

The confidence-level calculating portion 65 time sequentially stores the position of the feature region input from the feature-region identifying portion 68. Then, the confidence-level calculating portion 65 sequentially calculates the amount of movement in the position of the feature region by using the time at which the trigger signal is input from the identifying portion 63 as a starting point, and calculates the confidence level from the calculated amount of movement. The confidence level at this time is calculated in accordance with, for example, a function in which the confidence level linearly decreases with an increase in the amount of movement. The confidence-level calculating portion 65 outputs the calculated confidence level to the marking-image generating portion 66.

The marking-image generating portion 66 selects a hue that corresponds to the confidence level from a hue scale in which the confidence level calculated from the amount of movement is associated with the hue. By doing so, a combined image G having hues corresponding to the confidence level based on the amount of movement of the observation subject X at the positions of the high-luminance regions P is generated. Note that, as with the first embodiment, the marking-image generating portion 66 may set, instead of the hue, the saturation or the brightness in correspondence with the confidence level.

With this embodiment, it is possible to calculate, with even greater precision, the confidence level of the positions of the high-luminance regions P associated with the passage of time since the time at which the high-luminance regions P are identified. When the amount of movement of the feature region exceeds a predetermined threshold, the confidence-level calculating portion 65 may calculate the confidence level as being 0%. By doing so, it is possible to allow the user to quickly recognize that the confidence level of the property of the high-luminance region P has sufficiently deteriorated.

In the fluoroscopy apparatus 100 of this embodiment, in the case in which the confidence level is calculated by using both the amount of movement and the elapsed time since the time at which the high-luminance regions P are identified, the confidence-level calculating portion 65 should calculate one confidence level based on the elapsed time and another based on the amount of movement, and, among hue, brightness, and saturation, the confidence-level calculating portion 65 should set two of them for the high-luminance regions P, based on the two confidence levels. For example, the hue of the high-luminance regions P should be set from the confidence level based on the elapsed time, the brightness of the high-luminance regions P should be set from the confidence level based on the amount of movement, and a combined image G having the determined hue and brightness at the positions of the high-luminance regions P should be generated.

Figure 9:
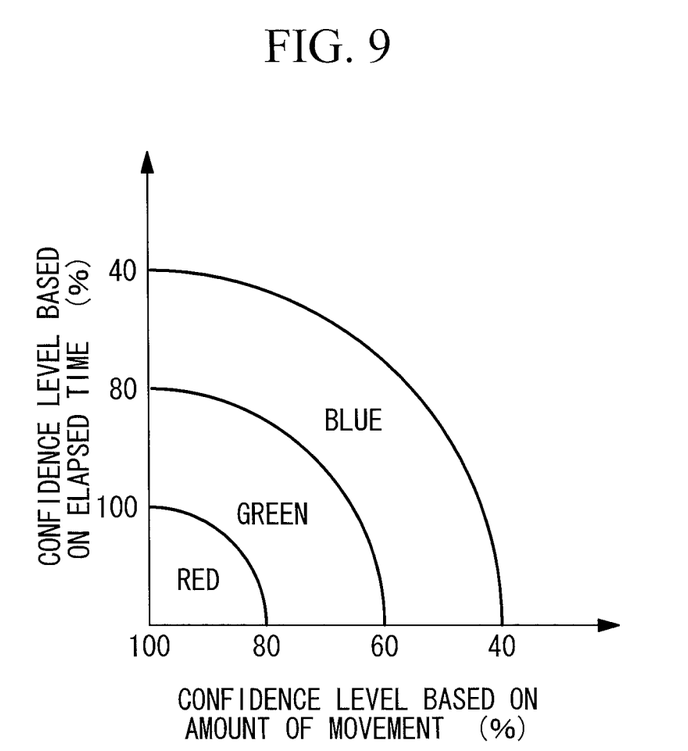
FIG. 9 is a diagram showing a hue space whose axes are the confidence level based on the elapsed time and the confidence level based on the amount of movement.

Alternatively, as shown in FIG. 9, from a two-dimensional hue space whose axes are the confidence level based on the elapsed time and the confidence level based on the amount of movement, the confidence-level calculating portion 65 may select a hue at a position determined based on the elapsed time measured by the timer and the calculated amount of movement.

Figure 10:
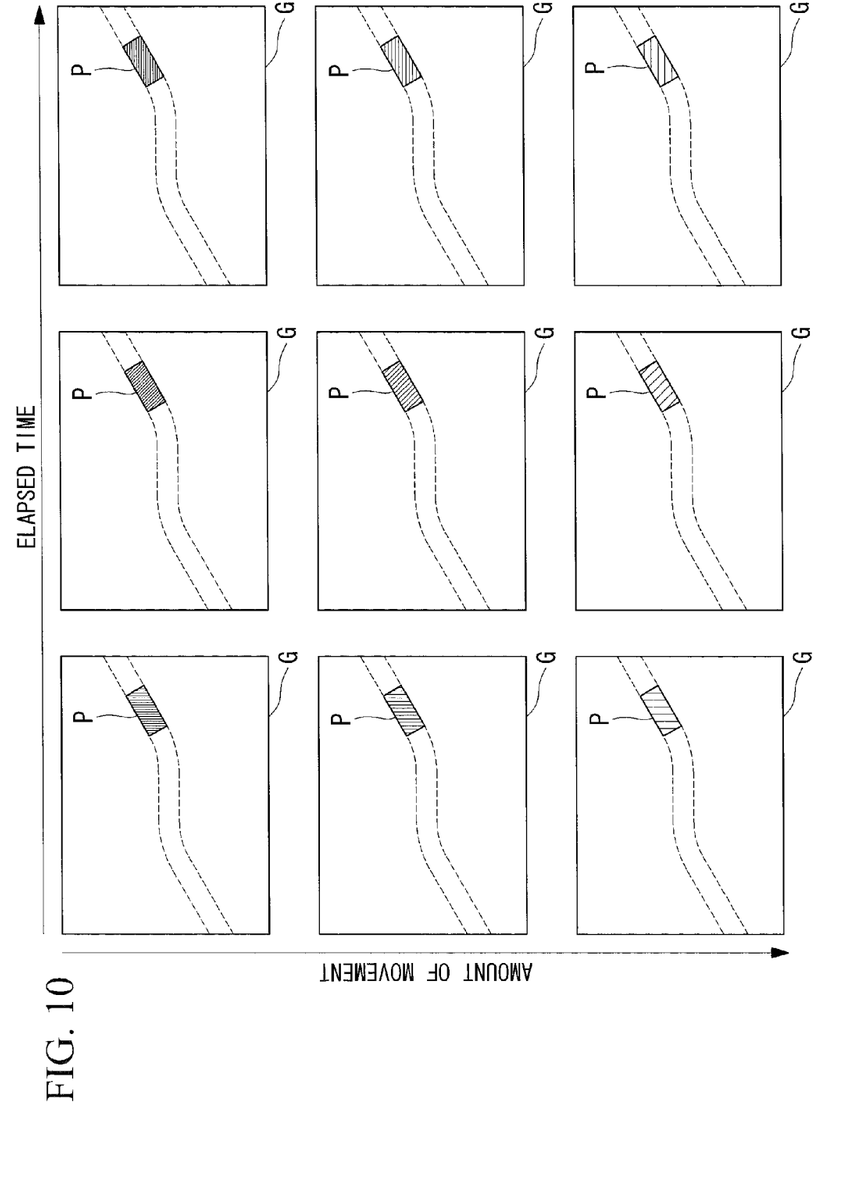
FIG. 10 is a diagram showing modifications of the combined images generated by the fluoroscopy apparatus in FIG. 8.

By doing so, as shown in FIG. 10, the confidence level of the positions and luminance values of the high-luminance regions P are shown by two types of information in the combined image G, and thus, it is possible to allow the user to recognize even more accurate confidence level of the positions and luminance values of the high-luminance regions P. In FIG. 10, different pitches of hatching indicate differences in the brightness.

In addition, in this embodiment, the feature-region identifying portion 68 may identify the position of a feature region in a Narrow Band Imaging (NBI) image, instead of the white-light image G1. In this case, the fluoroscopy apparatus 100 irradiates the observation subject X with blue and green light having sufficiently narrow wavelength bands, and is provided with another image-acquisition device that detects reflected light of these light beams coming from the observation subject X, as well as an NBI-image generating portion.

In addition, in this embodiment, the positions of the high-luminance regions P in the combined image G may be made to follow the movement of the feature region.

Specifically, together with the confidence level based on the amount of movement, the marking-image generating portion 66 receives the amount of movement of the feature region from the confidence-level calculating portion 65, moves the positions of the high-luminance regions P input from the storage portion 64 by the same amount as the amount of movement of the feature region, and generates a marking image G3 by applying the hues to the destination positions. By doing so, it is possible to reduce shifting of the positions of the high-luminance regions P in the combined image G with respect to the actual positions of the high-luminance regions P, caused by the movement of the inserted portion 2, and thus, it is possible to allow the user to recognize even more accurate positions of the high-luminance regions P.

In addition, in the fluoroscopy apparatus 100 according to this embodiment, when calculating the confidence level by using the elapsed time since the time at which the high-luminance regions P are identified, the confidence-level calculating portion 65 may store the feature region identified by the feature-region identifying portion 68 and the elapsed time in association with each other at the timing when the trigger signal is input from the identifying portion 63, and, thereafter, the confidence-level calculating portion 65 may measure the elapsed time only when the stored feature region is identified in the white-light image G1.

By doing so, for high-luminance regions P identified at different target portions, an independent elapsed time can be calculated for each target portion. Furthermore, when the feature region falls outside the viewing field of the white-light image G1, the measurement of the elapsed time is temporarily stopped, and the measurement of the elapsed time is restarted when the feature region appears again in the viewing field of the white-light image G1; therefore, it is possible to measure accurate elapsed time for the individual target portions.

At this time, in the flowchart shown in FIG. 5, instead of judging whether or not there is an update instruction from the user (Step S10), it is judged whether or not the feature region identified by the feature-region identifying portion 68 matches with the feature regions that are already stored. Then, when there is a match, the process advances to Step S7 after restarting the measurement of the elapsed time associated with the matching feature region among the stored feature regions. On the other hand, there is no match, the process advances to Step S4, and the identified feature region should newly be stored together with the positions of the high-luminance regions P.

Figure 11:
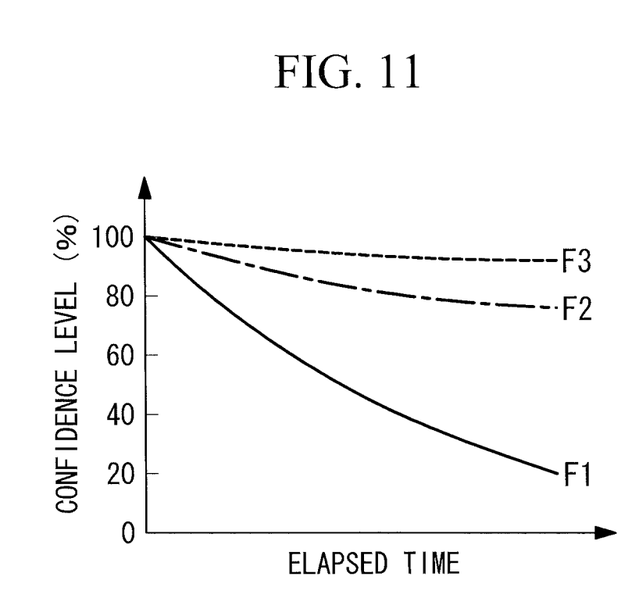
FIG. 11 is a graph showing another modification of the function for deriving the confidence level based on the elapsed time since the time at which the high-luminance region is identified.

In addition, in the above-described first and second embodiments, as shown in FIG. 11, the confidence-level calculating portion 65 may calculate the confidence level in accordance with a function based on bleaching characteristic of the fluorescent substance. In other words, by determining the relationship between the fluorescence intensity and the elapsed time since the time at which the irradiation of the fluorescent substance with the excitation light is started, a graph of the bleaching characteristic of the fluorescent substance is obtained, and the fluorescence intensity normalized by assuming the elapsed time in this graph to be the elapsed time measured by the timer and by assuming the fluorescence intensity at the time when irradiation with the excitation light is started to be 100% should be used as the confidence level.

In this case, by using the time at which the high-luminance region P is identified in the fluorescence image G2 for the first time as the starting point, the confidence-level calculating portion 65 continues to accumulate the elapsed time measured by the timer while the high-luminance regions P are being identified, without resetting the timer. The marking-image generating portion 66 generates a marking image G3 having luminance values in accordance with the confidence level calculated by the confidence-level calculating portion 65 at the positions of the high-luminance regions P. The functions based on the bleaching characteristic are set for a plurality of fluorescent substances F1, F2, and F3, and the configuration of the present invention may be such that the function to be used for calculating the confidence level is selected by the user specifying the fluorescent substance to be used by using an input portion (not shown).

By doing so, it is possible to make the luminance values of the high-luminance regions P displayed in the combined image G even more accurately reflect the current actual fluorescence intensity at the high-luminance regions P.

Note that, so as to make it possible to initialize the calculation process of the confidence level when the fluorescent substances are added to the observation subject X again after the fluorescence has bleached, the fluoroscopy apparatuses 1 and 100 may be configured so that the user can reset the elapsed time of the timer in the confidence-level calculating portion 65.

Figure 12:
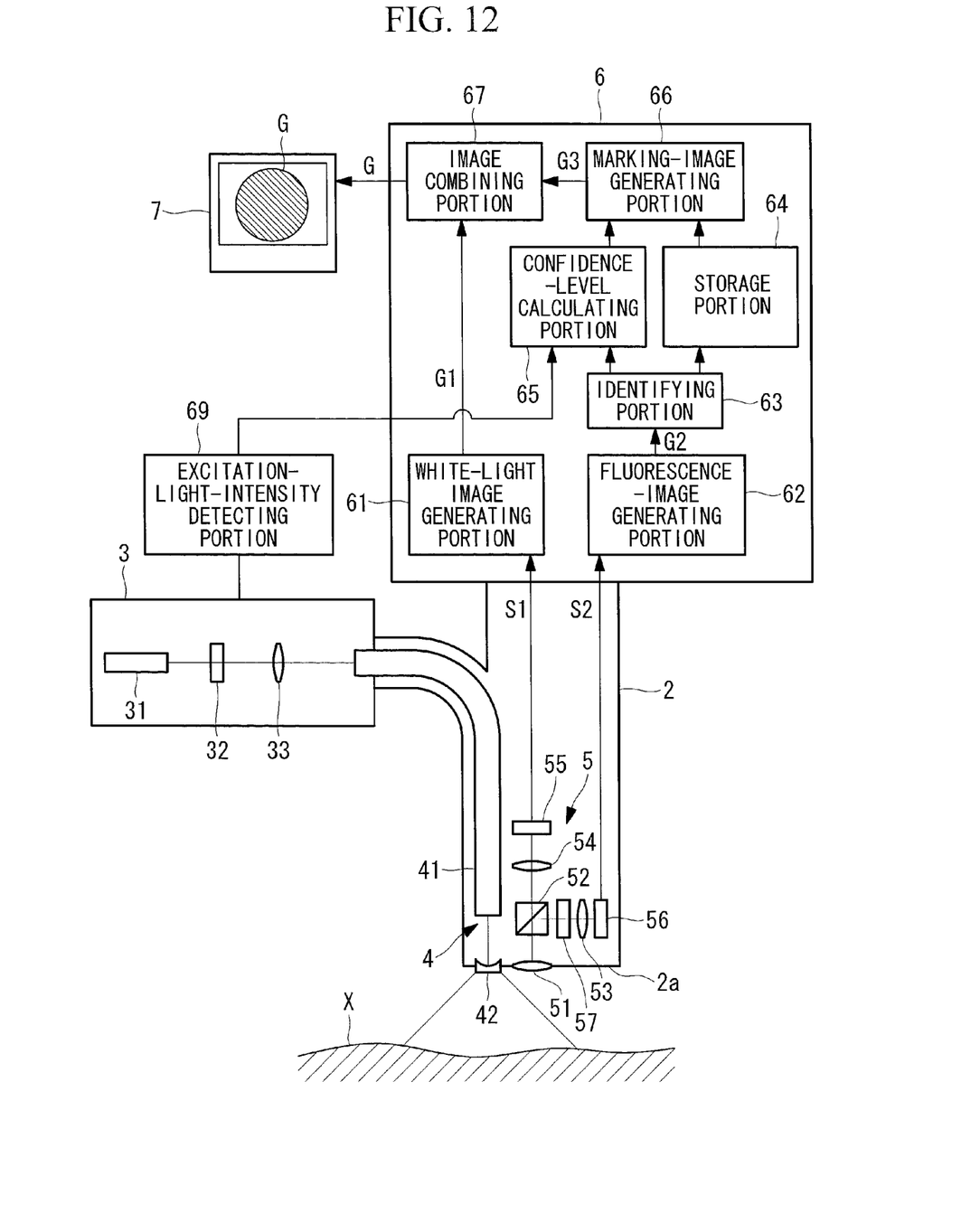
FIG. 12 is an overall configuration diagram showing another modification of the fluoroscopy apparatus in FIG. 1.

In addition, when calculating the confidence level in accordance with the function based on the bleaching characteristic of the fluorescent substance, as shown in FIG. 12, an excitation-light-intensity detecting portion 69 that detects the excitation light intensity may be provided, and the confidence-level calculating portion 65 may calculate the confidence level based on a product of the elapsed time measured by the timer and the excitation light intensity detected by the excitation-light-intensity detecting portion 69. FIG. 12 shows an example in which the excitation-light-intensity detecting portion 69 is applied to the configuration of the fluoroscopy apparatus 1 of the first embodiment. The excitation-light-intensity detecting portion 69 is provided with, for example, a half mirror that is provided between the filter 32 and the coupling lens 33 and that splits off a portion of the excitation light and a light-level meter that detects the light level of the portion of the excitation light split off by the half mirror.

Figure 13:
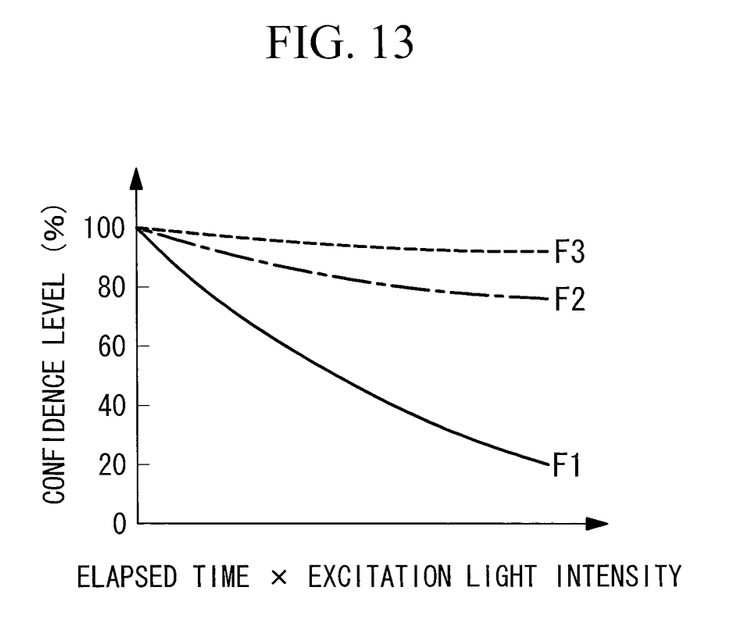
FIG. 13 is a graph showing a function for deriving the confidence level based on the product of the elapsed time since the time at which the high-luminance region is identified and the excitation light intensity.

FIG. 13 shows a function for deriving the confidence level from the product of the elapsed time and the excitation light intensity. Because the fluorescence intensity attenuates in accordance with the accumulated light level of the excitation light with which the fluorescent substance is irradiated, by calculating the confidence level from the product of the elapsed time and the excitation light intensity and by applying the luminance values based on the calculated confidence level to the positions of the high-luminance regions P, the present invention allows the user to recognize even more accurate fluorescence intensity at the actual high-luminance regions P.

Note that, instead of the excitation light intensity, the excitation-light-intensity detecting portion 69 may detect the intensity of the white light. Because there is a correlation between the intensities of the white light and the excitation light emitted from the same xenon lamp 31, it is possible to obtain the same effect as when the excitation light intensity is used. In this case, it is preferable that the intensity of the white light reflected at the observation subject X be detected as the intensity of the white light. In other words, the luminance value of the white-light image G1 should be detected as the intensity of the white light.

In addition, in the first and second embodiments, the configurations thereof may be such that the identification of the high-luminance regions P by the identifying portion 63 is started in response to an instruction from the user. For example, a user interface (not shown), such as a touch panel or the like, through which the user can input instructions related to the marking region and instructions for starting to generate the marking image G3 may be provided.

By doing so, processing from Steps S3 to S8 are performed at arbitrary timing selected by the user, and thus, it is possible to reduce the amount of calculation by generating the marking image G3 only when the user needs it.

In addition, in the first and second embodiments, the configurations thereof may be such that, when the confidence level falls below a predetermined threshold, for example, 50%, the high-luminance regions P in the combined image G are displayed in a flashing manner so as to allow the user to reliably recognize the deterioration of the confidence level.

In addition, in these embodiments, a switch that allows the user to switch between displaying and hiding the high-luminance regions P in the combined image G may be provided.

REFERENCE SIGNS LIST 1, 100 fluoroscopy apparatus
2 inserted portion
2a distal end
3 light source
31 xenon lamp
32 filter
33 coupling lens
4 illumination unit
41 light-guide fiber
42 illumination optical system
5 image-acquisition unit
51 objective lens
52 dichroic mirror
53, 54 focusing lens
55, 56 image-acquisition device
57 excitation light cut filter
6 image processing unit
61 white-light image generating portion (reference-image generating portion)
62 fluorescence-image generating portion
63 identifying portion
64 storage portion
65 confidence-level calculating portion (detecting portion)
66 marking-image generating portion (display-image generating portion)
67 image combining portion
68 feature-region identifying portion
69 excitation-light-intensity detecting portion
7 display portion
X observation subject
G1 white-light image (reference image)
G2 fluorescence image
G3 marking image (display image)
G combined image
P high-luminance region

The invention claimed is:

1. A fluoroscopy apparatus comprising:
a light source that radiates excitation light onto an observation subject;
a fluorescence-image generating portion that generates a fluorescence image by capturing fluorescence generated at the observation subject due to irradiation with the excitation light from the light source;
an identifying portion that identifies a position of a high-luminance region that has a luminance value equal to or greater than a predetermined threshold in the fluorescence image generated by the fluorescence-image generating portion;
a storage portion that stores the position of the high-luminance region identified by the identifying portion;
a detecting portion that detects an amount of change in a physical quantity, which can possibly act as a cause of changes in a property of the high-luminance region, starting from a time at which the position of the high-luminance region is identified by the identifying portion;
a confidence-level calculating portion that calculates a confidence level of the property of the high-luminance region identified by the identifying portion based on the amount of change detected by the detecting portion; and
a display-image generating portion that generates a display image in which the display mode at the position of the high-luminance region stored in the storage portion is set in accordance with the confidence level calculated by the confidence-level calculating portion.

2. The fluoroscopy apparatus according to claim 1, wherein the detecting portion detects, as the amount of change in the physical quantity, an elapsed time since the time at which the position of the high-luminance region is identified by the identifying portion.

3. The fluoroscopy apparatus according to claim 1,
wherein the light source radiates reference light onto the observation subject together with the excitation light;
a reference-image generating portion that generates a reference image by capturing return light returning from the observation subject due to the irradiation with the reference light from the light source is provided; and
the detecting portion detects, as the amount of change in the physical quantity, an amount of movement of the observation subject in the reference image generated by the reference-image generating portion since the time at which the position of the high-luminance region is identified by the identifying portion.

4. The fluoroscopy apparatus according to claim 2, wherein the confidence-level calculating portion calculates the confidence level in accordance with a function that decreases with an increase in the amount of change in the physical quantity.

5. The fluoroscopy apparatus according to claim 3, wherein the confidence-level calculating portion calculates the confidence level in accordance with a function that decreases with an increase in the amount of change in the physical quantity.

6. The fluoroscopy apparatus according to claim 2, wherein the confidence-level calculating portion calculates the confidence level in accordance with a function based on a bleaching characteristic of the fluorescence intensity, which decreases with an increase in the elapsed time.

7. The fluoroscopy apparatus according to claim 6,
wherein the detecting portion detects the excitation light intensity in addition to the elapsed time; and
the confidence-level calculating portion calculates the confidence level in accordance with a function based on the bleaching characteristic of the fluorescence, which decreases with an increase in a product of the elapsed time and the excitation light intensity.

8. The fluoroscopy apparatus according to claim 4, wherein the function is set for each observation subject.

9. The fluoroscopy apparatus according to claim 5, wherein the function is set for each observation subject.

10. The fluoroscopy apparatus according to claim 6, wherein the function is set for each observation subject.

11. The fluoroscopy apparatus according to claim 7, wherein the function is set for each observation subject.

12. The fluoroscopy apparatus according to claim 1, wherein the confidence-level calculating portion calculates the confidence level as being 0% when the amount of change in the physical quantity is equal to or greater than a predetermined threshold.

13. The fluoroscopy apparatus according to claim 1, wherein the storage portion updates the position of the stored high-luminance region to a position of a newly identified high-luminance region, each time the position of the high-luminance region is identified by the identifying portion.

14. The fluoroscopy apparatus according to claim 1, wherein the display-image generating portion applies hue, brightness, or saturation in accordance with the amount of change in the physical quantity to the position of the high-luminance region.

* * * * *